(12) United States Patent
Kopkalli et al.

(10) Patent No.: US 9,242,910 B2
(45) Date of Patent: Jan. 26, 2016

(54) PROCESS TO MANUFACTURE 2-CHLORO-1,1,1,2-TETRAFLUOROPROPANE (HCFC-244BB)

(71) Applicant: Honeywell International, Inc., Morristown, NJ (US)

(72) Inventors: Haluk Kopkalli, Staten Island, NY (US); Daniel C. Merkel, Orchard Park, NY (US); Ron Joseph Roof, Center Valley, PA (US)

(73) Assignee: Honeywell International Inc., Morristown, NJ (US)

( * ) Notice: Subject to any disclaimer, the term of this patent is extended or adjusted under 35 U.S.C. 154(b) by 7 days.

(21) Appl. No.: 14/208,411

(22) Filed: Mar. 13, 2014

(65) Prior Publication Data

US 2014/0343331 A1    Nov. 20, 2014

Related U.S. Application Data

(60) Provisional application No. 61/790,206, filed on Mar. 15, 2013.

(51) Int. Cl.
| | | |
|---|---|---|
| C07C 17/25 | (2006.01) | |
| C07C 17/08 | (2006.01) | |
| C07C 17/087 | (2006.01) | |
| C07C 17/20 | (2006.01) | |
| C07C 17/23 | (2006.01) | |

(52) U.S. Cl.
CPC ............... *C07C 17/08* (2013.01); *C07C 17/087* (2013.01); *C07C 17/206* (2013.01); *C07C 17/23* (2013.01); *C07C 17/25* (2013.01)

(58) Field of Classification Search
CPC ........................................................ C07C 17/25
USPC .................................. 570/158, 155, 156, 157
See application file for complete search history.

(56) References Cited

U.S. PATENT DOCUMENTS

| | | |
|---|---|---|
| 7,102,040 B2 | 9/2006 | Chiu et al. |
| 8,084,653 B2 | 12/2011 | Tung et al. |
| 8,258,355 B2 | 9/2012 | Merkel et al. |
| 2009/0240090 A1 | 9/2009 | Merkel et al. |
| 2010/0036179 A1 | 2/2010 | Merkel et al. |
| 2011/0105807 A1 | 5/2011 | Kopkalli et al. |
| 2011/0201853 A1 | 8/2011 | Tung et al. |
| 2011/0218369 A1 | 9/2011 | Elsheikh et al. |
| 2011/0270001 A1 | 11/2011 | Ishihara et al. |
| 2012/0065437 A1 | 3/2012 | Merkel et al. |
| 2012/0123172 A1 | 5/2012 | Hibino et al. |
| 2012/0271070 A1 | 10/2012 | Wang et al. |
| 2012/0296128 A1 | 11/2012 | Merkel et al. |

FOREIGN PATENT DOCUMENTS

WO    WO2013007906 A1    1/2013

OTHER PUBLICATIONS

International Search Report and Written Opinion in corresponding PCT/US2014/025325, dated Jul. 10, 2014.

*Primary Examiner* — Elvis O Price

(74) *Attorney, Agent, or Firm* — Scully, Scott, Murphy & Presser, P.C.

(57) ABSTRACT

The invention relates to a process to produce HCFC-244bb from HCFO-1233xf wherein, in one embodiment, co-feed species HFC-245cb is added to the reaction at a pressure of at least about 100 psig; and in another embodiment it is added to maintain a mole ratio of HFC-245cb to HCFO-1233xf of between about 0.005:1 to about 1:1. The HFC-245cb may be added as recycled by-product of the reaction and/or added as fresh feed. The HFC-245cb provides elevated pressures to the reaction thereby facilitating reactor operation, mixing and HCFC-244bb product removal. Other co-feed species are also disclosed.

28 Claims, 1 Drawing Sheet

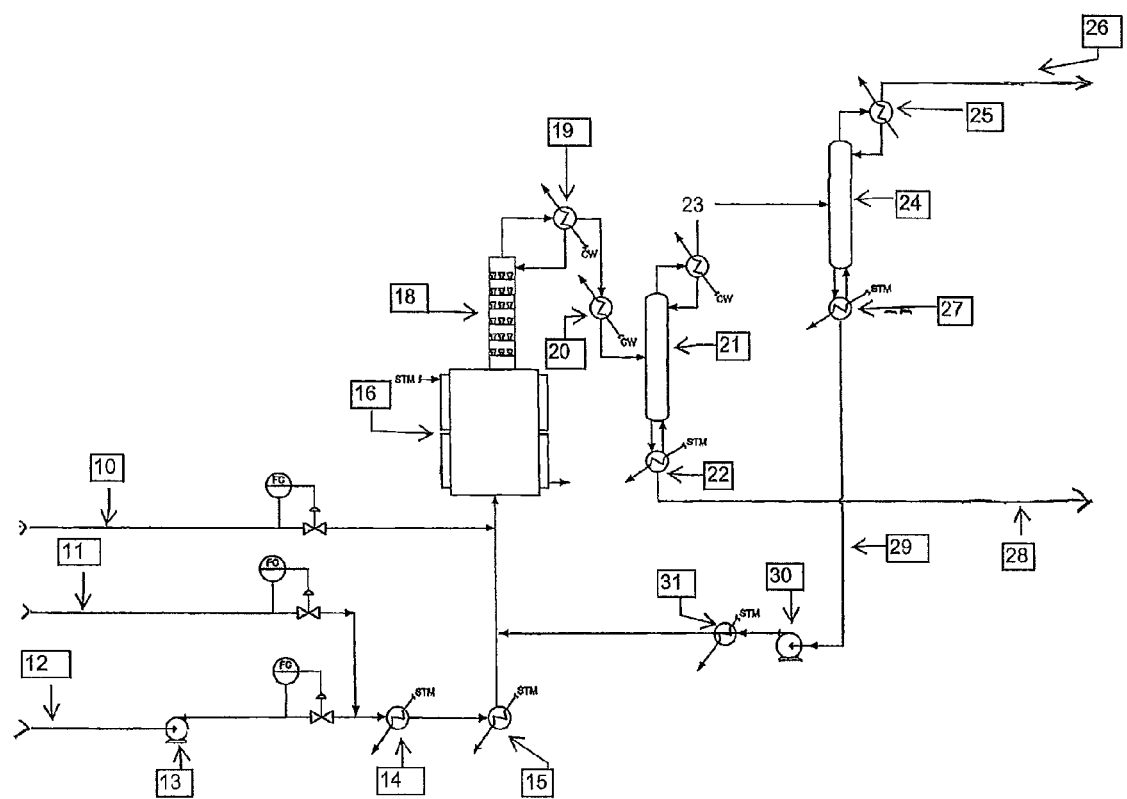

PROCESS TO MANUFACTURE 2-CHLORO-1,1,1,2-TETRAFLUOROPROPANE (HCFC-244BB)

FIELD OF THE INVENTION

The present invention relates to a process to prepare 2-chloro-1,1,1,2-tetrafluoropropane (HCFC-244bb) from 2-chloro-3,3,3,-trifluoropropene (HCFO-1233xf) wherein a co-feed species such as 1,1,1,2,2-pentafluoropropane (HFC-245cb) is added to the reaction to facilitate process operation. The process is further useful in preparing 2,3,3,3-tetrafluoropropene (HFO-1234yf).

BACKGROUND OF THE INVENTION

Fluorocarbons, particularly fluorinated olefins, as a class, have many and varied uses, including as chemical intermediates and monomers. In particular, these products are useful as refrigerants, monomers or intermediates for preparing refrigerants, particularly those identified as having low global warming potential.

With concerns over global warming, hydrofluoroolefins (HFOs) are being commercialized as substitutes for chlorofluorocarbons (CFCs), hydrochlorofluorocarbons (HCFCs) and hydrofluorocarbons (HFCs) for use as refrigerants, heat transfer agents, blowing agents, monomers and propellants because HFOs do not deplete the ozone layer and have low global warming potential. Some HFOs are prepared by multiple steps that involve fluorinating a chlorinated organic compound with a fluorination agent such as hydrogen fluoride in the presence of a fluorination catalyst. These reactions may be conducted in either the liquid or gas phase or a combination of these. Among processes to manufacture 2,3,3,3-tetrafluoropropene (HFO-1234yf), the following reaction sequence is known:

Step 1 wherein TCP is 1,1,2,3-tetrachloropropene, or CCl₂=CClCH₂Cl and/or 2,3,3,3,-tetrachloropropene or CH₂=CClCCl₃; and 1233xf is 2-chloro-3,3,3,-trifluoropropene, or CH₂=CClCF₃;

Step 2 wherein 244bb is 2-chloro-1,1,1,2-tetrafluoropropane, or CH₃CClFCF₃.

A by-product of Step 2 can also form as follows: 1233xf+ 2HF→245cb+HCl, where 245cb is 1,1,1,2,2-pentafluoropropane, or CH₃CF₂CF₃; and

Step 3 wherein 1234yf is 2,3,3,3-tetrafluoropropene, or CH₂=CFCF₃.

In various practices, Step 1 takes place in the gas phase in the presence of a fluorination catalyst, Step 2 takes place in the liquid phase in the presence of a fluorination catalyst, and Step 3 takes place in the gas phase in the presence or absence of a dehydrochlorination catalyst.

For Step 2 of the above process, herein referred to as "the Step (2) reaction," liquid phase fluorination is preferred because the reaction can be controlled at relatively lower temperatures, which, in turn, results in less by-product formation due, e.g., to decomposition. In the liquid phase fluorination of HCFO-1233xf to produce HCFC-244bb, no HCl, or at least no meaningful amount, is produced because the reaction is strictly a hydrofluorination reaction where HF adds across the double bond of 1233xf. This lack of meaningful HCl by-product formation is unique when compared to other well-known liquid phase fluorination reactions that produce CFCs (e.g. CFC-12), HCFCs (e.g. HCFC-22, HCFC-142b), and HFCs (e.g. HFC-143a, HFC-245fa). This is because these reactions involve a halogen exchange, in whole or in part. That is, F⁻ replaces a Cl⁻ on the molecule.

However, it has been found that the inadequate HCl formation has consequences that are adverse to processing. For example, it has been found that because inadequate HCl is produced in the reaction of HCFO-1233xf to HCFC-244bb, there is less mixing in the reactor, which can decrease conversion and also promote by-product formation. In addition, the reactor itself is more difficult to control; among other reasons for this is difficulty in achieving and/or maintaining adequately elevated pressures in the reactor needed to help carry out the reaction to form HCFC-244bb. It has been found in this regard that the formation of HCl in sufficient quantities correlates with the generation of higher pressure, and that the lack of sufficient HCl causes deficient pressure. Other advantages ascribable to the adequate formation of HCl have been found as well. For example, because it is non-condensable at the desired reaction conditions, adequate HCl formation would also increase mixing in the reactor; also, it would readily be carried out in the overhead of the catalyst stripper, and would help carry out the fluorinated product.

Thus there is a need to compensate for the inadequate formation of HCl formation in Step (2) of the reaction.

SUMMARY OF THE INVENTION

It has been found that varying amounts of an overfluorinated side-product, HFC-245cb, forms in Step (2) of the reaction, and that HFC-245cb is inert in this reaction system, and is non-condensable under certain reaction conditions and, thus, is a suitable mixing gas for the Step (2) reaction and provides the above described benefits otherwise generally ascribable to HCl.

In one practice, in Step (2) of the reaction, HFC-245cb is co-fed to the reactor, either as recycle and/or as fresh feed, along with the HF and HCFO-1233xf. The reactor and catalyst stripper runs like a typical liquid phase fluorination reaction that produce CFCs, HCFC's, and HFCs as described above. The HFC-245cb as used in the invention enables the reaction to achieve, and run at, relatively elevated pressures; it further increases mixing in the reactor; and it readily leaves the reactor in the overhead of the catalyst stripper carrying with it the desired product, HCFC-244bb. The HFC-245cb co-feed is essentially inert, does not participate in the fluorination reaction, and produces little or no unwanted by-products.

In the practice of the invention, any source of HFC-245cb can be used in the reaction. Preferably HFC-245cb is produced in situ in the Step (2) reaction, recovered and recycled to the Step (2) reaction. In this regard, all or only a portion of the HFC-245cb produced in this step is co-fed into the liquid phase fluorination reactor that produces HCFC-244bb. The amount of HFC-245cb produced in Step (2) of the reaction may be adjusted by varying, among others, the reaction temperature, catalyst concentration, etc. Optionally, the HFC-245cb may be added to Step (2) of the reaction as fresh feed. Combinations of recycle and fresh feed may be used.

In other embodiments, other compounds can be used in lieu of HFC-245cb or in addition thereto. These additional compounds are inert and recoverable materials. By recoverable, it is meant a species that can be recycled without causing yield loss. In this regard, inert gases such as nitrogen or argon would not be useful as they would cause an unacceptable yield loss or require large capital expenditure to reduce yield losses. Non-exclusive examples of recoverable compounds include CFC-12 (dichlorodifluoromethane), CFC-13 (chlorotrifluoromethane), CFC-14 (tetrafluoromethane), HCFC-22 (chlorodifluoromethane), HCFC-23 (trifluoromethane), HFC-32 (difluoromethane), HCC-40(chloromethane) HFC-41 (fluoromethane), CFC-115(chloropentafluoroethane), FC-116 (hexafluoroethane), HCFC-124 (2-chloro-1,1,1,2-tetrafluoroethane), HFC-125 (pentafluoroethane), HFC-134a (1.1.1.2-tetrafluoroethane), HFC-143a (1,1,1-trifluoroethane), HFC-152a (1,1-difluoroethane), HFC-161 (fluoroethane), FC-218 (octafluoropropane), HFC-227ea (1,1,1,2,3,3,3-heptafluoroethane), $SF_6$ (Sulfur hexafluoride). In general, any species inert (by itself or in combination) in the Step (2) reaction system may be utilized provided the normal boiling point of the species is less than about 0° C.; for example, less than about −10° C. In another embodiment, the boiling point of the compound that can replace HFC-245cb is less than about −15° C. To be useful the species should be separable and recoverable from 244bb via conventional means such as distillation and the like.

In one embodiment, the invention is to a process to prepare 2-chloro-1,1,1,2-tetrafluoropropane (244bb) comprising (a) contacting 2-chloro-3,3,3,-trifluoropropene (1233xf) with HF in a reaction zone under conditions effective to form 244bb; and (b) adding 1,1,1,2,2-pentafluoropropane (245cb) to the reaction zone at so as to promote mixing and elevate pressure in the reaction zone. The 245cb may be added at start up or at any time during the reaction. Preferably, the 245cb is added at a pressure of at least 100 psig; more preferably, at a pressure of between about 100 psig to about 500 psig; still more preferably, at a pressure of between about 120 psig and about 300 psig. In another embodiment, the 245cb is added to maintain, in the reaction zone, a mole ratio of 245cb to 1233xf of between about 0.005:1 to about 1:1; preferably, this mole ratio is between about 0.01:1 to about 0.5:1; more preferably, this mole ratio is between about 0.04:1 to about 0.25:1.

BRIEF DESCRIPTION OF THE DRAWING

The FIGURE depicts an embodiment of a process flow scheme of the invention whereby 245cb produced in Step (2) of the reaction is separated from the product mixture and recycled back to the reactor.

DESCRIPTION OF THE INVENTION

The foregoing summary and general description of the invention and the ensuing detailed description are exemplary and explanatory and are not restrictive of the invention, as defined in the appended claims. Other features and embodiments and modifications will be apparent from the present description and are within the scope of the invention. The entire contents of U.S. Pat. Nos. 7,102,040, 8,258,355, and 8,084,653 are incorporated herein by reference.

In one embodiment, the invention provides a process for the production of 2-chloro-1,1,1,2-tetrafluoropropane (244bb) which comprises reacting 2-chloro-3,3,3-trifluoropropene (1233xf) with hydrogen fluoride (HF), in a reaction zone, such as a liquid phase reaction vessel, in the presence of 1,1,1,2,2-pentafluoropropane (HFC-245cb) as well as any HCl produced by the reaction of HCFO-1233xf with HF to form HFC-244bb, and a liquid phase fluorination catalyst, wherein the HFC-245cb is added to the reaction zone so as to elevate the pressure; preferably, the HFC-245cb is added at a pressure of about 100 psig or more. Preferably, the reaction is conducted continuously. In another embodiment, the invention is a process to prepare 2-chloro-1,1,1,2-tetrafluoropropane (244bb) comprising feeding, to a reaction zone, 2-chloro-3,3,3,-trifluoropropene (1233xf), HF, and 1,1,1,2,2-pentafluoropropane (245cb) under conditions effective to form 244bb wherein the mole ratio of 245cb to 1233xf in the reaction zone is between about 0.005:1 to about 1:1.

Liquid phase fluorination, as described herein, uses and generates corrosive compounds, such as hydrogen fluoride, hydrogen chloride, and Lewis acid catalysts, which form super acids. These super acids tend to corrode the reactor vessel in which the reaction is conducted, even reactors comprised of corrosion-resistant materials such as Inconel™ 600, NAR25-50MII, Hastelloy™ C, Hastelloy™ G-30, duplex stainless steel, and Hastelloy™ C-22. Due to the corrosive nature of the reaction mixture, the reactor for the Step (2) reaction is preferably lined with a fluoropolymer such as PFA or PTFE or other suitable material.

In one practice of the invention, a liquid phase catalyst, as e.g. described below, is charged into a fluorination reactor prior to heating the reactor. Any reactor suitable for a fluorination reaction may be used in the invention; such liquid phase fluorination reactors are well known in the art. Then, the HF, HFC-245cb and the HCFO-1233xf are fed to the reactor after the reactor reaches the desired temperature. In the preferred embodiment, the reaction is conducted at a temperature of from about 30° C. to about 200° C., more preferably from about from about 50° C. to about 150° C., and still more preferably from about 75° C. to about 125° C. The pressure of the reaction varies depending on the temperature, quantity of HFC-245cb and hydrogen fluoride used, and conversion of HCFO-1233xf. Convenient operating pressure ranges from about 5 psia to about 200 psia, and preferably from 30 to about 175 psia, and most preferably about 60 psia to about 150 psia. The initial amount of HFC-245cb may be produced in the same reactor by selecting the appropriate reaction conditions or may be procured elsewhere.

In the preferred embodiment, the catalyst is present in an amount of from about 2% to about 99%, and preferably from about 5% to about 90%, and most preferably from about 10% to about 80%, based on the mole percent of HF inventory in the reactor. Fluorination catalysts having a purity of at least 98% are preferred.

Based on reaction stoichiometry, the required mole ratio of HF to HCFO-1233xf is at least equal to the number of double bonds in the starting organic material and preferably is present in an excess. In the preferred embodiment, the mole ratio of HF to HCFO-1233xf ranges from at least about 1:1 to about 50:1, more preferably from about 1:1 to about 30:1 and most preferably from about 2:1 to about 15:1. Any water in the HF will typically react with and deactivate the catalyst. Therefore, substantially anhydrous HF is preferred. By "substantially anhydrous" is meant that the HF contains less than about 0.05 weight % water and preferably contains less than about 0.02 weight % water. However, one of ordinary skill in the art will appreciate that the presence of water in the catalyst can be compensated for by increasing the amount of catalyst used.

The liquid phase fluorination reaction is conducted with a sufficient amount of HFC-245cb and/or other co-feed species to elevate the pressure in the reactor, above the pressure achieved compared to a similar liquid phase reaction without adding HFC-245cb and/or other co-feed species. In the preferred embodiment, the mole ratio of HFC-245cb and/or other co-feed species to HCFO-1233xf ranges from about 0.005:1 to about 1:1, more preferably from about 0.01:1 to about 0.5:1 and most preferably from about 0.04:1 to about 0.25:1. The HFC-245cb and/or other co-feed species is added into the reaction from an external source at a pressure of about 100 psig or more; preferably from about 100 psig to about 500 psig, and more preferably from about 120 psig to about 300 psig. It may be supplied as a liquid and vaporized at the required pressure by the use of a heating medium such as steam or it may be supplied as a vapor and compressed to the required pressure.

Any liquid phase fluorination catalyst may be used in the invention. A non-exhaustive list includes Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Liquid phase fluorination catalyst comprises $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

The resulting HCFC-244bb, as well as HF, HFC-245cb or other co-feed species, and HCl if any, may be recovered from the reaction mixture via any separation or purification method known in the art such as neutralization and distillation. The HCFC-244bb can be used in pure form, or optionally in partially pure form or impure form with the entire effluent from the HCFC-244bb production step used as an intermediate in the production of 2,3,3,3-tetrafluoropropene HFO-1234yf. The HFC-245cb or other co-feed species may be recovered, stored and recycled back to the Step (2) reaction. The process of the invention may be carried out either in a batch or continuous mode. In a continuous process, the HCFO-1233xf, HFC-245cb or other co-feed species and HF are preferably fed simultaneously to the reactor after the reactor reaches the desired temperature. The temperature and pressure of the fluorination reaction remain essentially the same for both the batch and continuous modes of operation. The residence time or contact time, varies from about 1 second to about 2 hours, preferably from about 5 seconds to about 1 hour and most preferably from about 10 seconds to about 30 minutes. A sufficient quantity of catalyst must be present to effect the fluorination in the residence times described above. In a continuous mode of operation, HF, HCFC-244bb, HFC-245cb or other co-feed species and any HCl that may be formed are continuously removed from the reactor.

Without limitation, the FIGURE depicts an embodiment of a flow scheme for the invention. In the FIGURE, feed lines 10, 11 and 12 respectively represent chlorine ($Cl_2$), HF and 1233xf wherein reactor feed pump 13, vaporizer 14, and superheater 15 are upstream of the Step (2) reactor 16. As shown, a product stream containing, among other things, 244bb and 245cb, is removed from reactor 16 as overhead passing through catalyst stripper 18 and condenser 19 prior to separation column 21, which column has pre-cooler 20, condenser 23, and reboiler 22; the bottoms 28 from which reboiler 22 contains crude 244bb ultimately sent to a recovery process. The overhead from column 21 is fed to the 245cb recycle column 24 having condenser 25, from which is derived waste gas 26, and reboiler 27. The compound 245cb is substantially recovered from column 24 as bottoms stream 29 which is then recycled back to reactor 16 passing through pump 30 and vaporizer 31.

HCFO-1233xf is useful as an intermediate in the production of 2,3,3,3-tetrafluoropropene (HFO-1234yf). In a process of preparing HCFO-1233xf, precursor reagents are fluorinated with hydrogen fluoride. This may be done, for example, by the gas or liquid phase catalytic fluorination of $CCl_2$=$CClCH_2Cl$ and/or $CH_2$=$CClCCl_3$ and/or $CCl_3CHClCH_2Cl$ with HF to yield HCFO-1233xf. The reaction products of such precursors include HCFO-1233xf, unreacted HF, HCl, and other by-products which are then available for separation into component parts.

In one embodiment in this regard, the invention provides a process for the production of 2,3,3,3-tetrafluoropropene which comprises (i) continuously reacting 2-chloro-3,3,3,-trifluoropropene with hydrogen fluoride, in a liquid phase reaction and co-feeding HFC-245cb or other co-feed species, in the presence of a liquid phase fluorination catalyst to produce a composition comprising 2-chloro-1,1,1,2-tetrafluoropropane, wherein the HFC-245cb or other co-feed species is added into the reaction at a pressure of about 100 psig or more; and then (ii) dehydrohalogenating the 2-chloro-1,1,1,2-tetrafluoropropane under conditions effective to produce 2,3,3,3-tetrafluoropropene.

The process of the invention may be employed, for example, as part of a larger process to make compounds such as 2,3,3,3-tetrafluoropropene (1234yf). For example, the process of the invention can be the second step of the three-step process to make 1234yf as described above. In a preferred embodiment in this regard, the present invention comprises a step of an integrated manufacturing process for making 2,3,3,3-tetrafluoropropene. The preferred starting material for this process is one or more chlorinated compounds according to Formulae I, II and/or III:

$CX_2$=$CCl$—$CH_2X$ (Formula I)

$CX_3$—$CCl$=$CH2$ (Formula II)

$CX_3$—$CHCl$—$CH_2X$ (Formula III)

wherein X is independently selected from F, Cl, Br, and I, provided that at least one X is not fluorine; Preferably, these compounds contain at least one chlorine, more preferably a majority of X is chlorine, and even more preferably all X is chlorine. Preferably, the method generally comprises at least three reaction steps.

Step (1):

This reaction, hereinafter referred to as "the Step (1) reaction," may be conducted in any reactor suitable for a vapor or liquid phase fluorination reaction. Preferably the reactor is constructed from materials which are resistant to the corrosive effects of hydrogen fluoride and catalyst such as Hastelloy™, Inconel™, Monel™ and vessels lined with fluoropolymers. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures. Combinations of catalysts suitable for the present invention nonexclusively include $Cr_2O_3$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

The reactor is preheated to the fluorination reaction temperature while anhydrous HF is fed to the reactor. A starting composition including one or more compounds having Formula (I), (II) or (III), preferably 1,1,2,3-tetrachloropropene (HCC-1230xa, or TCP) and/or 2,3,3,3-tetrachloropropene (HCC-1230xf, or TCP) and/or 1,1,1,2,3-pentachloropropane (240db) and HF may be fed to the reactor at any convenient temperature and pressure. In a preferred embodiment either or both of the TCP (HCC-1230xa and/or HCC-1230xf) and/or HCC-240db and the HF are pre-vaporized or preheated to a temperature of from about 30° C. to about 300° C. prior to entering the reactor. In another embodiment, the TCP and/or HCC-240db and HF are vaporized in the reactor. The HF and TCP and/or HCC-240db feeds are then adjusted to the desired mole ratio. The HF to TCP and/or HCC-240db mole ratio preferably ranges from about 3:1 to about 100:1; more preferably from about 4:1 to about 50:1 and most preferably from about 5:1 to about 20:1.

The vapor phase fluorination reaction is conducted at a preferred temperature ranging from about 80° C. to about 400° C.; more preferably from about 100° C. to about 350° C. and most preferably from about 200° C. to about 330° C. Reactor pressure is not critical and can be superatmospheric, atmospheric or under vacuum. The vacuum pressure can be from about 5 torr (0.0966 psia) to about 760 torr (14.69 psia). During the vapor phase fluorination reaction, TCP and/or HCC-240db and HF are reacted in a vapor phase in the presence of the fluorination catalyst. The reactant vapor is allowed to contact the fluorination catalyst for from about 1 to 120 seconds or more preferably from about 1 to 20 seconds. For purposes of this invention, "contact time" is the time required for the gaseous reactants to pass through the catalyst bed assuming that the catalyst bed is 100% void.

In the preferred embodiment, the process flow is in the down direction through a bed of the catalyst. Before each use, the catalyst is preferably dried, pre-treated and activated. It may also be advantageous to periodically regenerate the catalyst after prolonged use while in place in the reactor. Pre-treatment can be done by heating the catalyst to about 250° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as using an oxidizing agent such as $O_2$ or chlorine ($Cl_2$). For example, passing air or air diluted with nitrogen over the catalyst at temperatures of from about 100° C. to about 400° C., preferably from about 200° C. to about 375° C., for from about 8 hours to about 3 days, depending on the size of the reactor.

In one embodiment, the HCFO-1233xf may be recovered from the fluorination reaction product mixture comprised of unreacted starting materials, by-products including HCl, HF, and the HCFO-1233xf by any means known in the art, such as by distillation. For example, the distillation may be preferably conducted in a standard distillation column at a pressure which is less than about 300 psig, preferably less than about 200 psig and most preferably less than 150 psig. The pressure of the distillation column inherently determines the distillation operating temperature. HCl may be recovered by operating the distillation column at from about −40° C. to about 25° C., preferably from about −40° C. to about −20° C. HCFO-1233xf may be recovered by operating the distillation column at from about −10° C. to about 60° C. Single or multiple distillation columns may be used. The distillate portion includes substantially all the HCl, and HCFO-1233xf produced in the reaction and the bottoms portion includes the HF and other impurities.

Step (2):

In the second step, the process of the present invention as described herein is employed. For example, HFCO-1233xf produced in Step (1) is combined with HF, HFC-245cb or other co-feed species, by recycle and/or fresh feed, under conditions effective to convert the HCFO-1233xf into the HCFC-244bb as described above.

Step (3):

The HCFC-244bb produced in Step (2) is then dehydrohalogenated under conditions effective to produce 2,3,3,3-tetrafluoropropene (HFO-1234yf). Preferably the dehydrohalogenating step comprises a gas or vapor phase catalytic reaction. The catalytic conversion of HCFC-244bb, hereinafter referred to as "the Step (3) reaction," is conducted under conditions effective to dehydrochlorinate HCFC-244bb to produce 2,3,3,3-tetrafluoropropene (HFO-1234yf. Preferably dehydrochlorination of HCFC-244bb is done in a vapor phase, and more preferably in a fixed-bed reactor in the vapor phase. The dehydrohalogenation reaction may be conducted in any suitable reaction vessel or reactor, but it should preferably be constructed from materials which are resistant to the corrosive effects of hydrogen chloride (to the extent that such material is formed under the dehydrohalogenation conditions) such as nickel and its alloys, including Hastelloy™, Inconel™, Incoloy™, and Monel™ or vessels lined with fluoropolymers and may employ single or multiple tubes packed with a dehydrohalogenation catalyst.

The catalysts may be metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel™ 400, Inconel™ 825, Inconel™ 600, and Inconel™ 625.

The HCFC-244bb is introduced into the reactor either in pure form, partially purified form, or as part of the reactor effluent from the preceding step. The HCFC-244bb may optionally be fed with an inert gas diluent such as nitrogen, argon, or the like. In a preferred embodiment of the invention, the HCFC-244bb is pre-vaporized or preheated prior to entering the reactor. Alternately, the HCFC-244bb is vaporized inside the reactor. Useful reaction temperatures may range from about 100° C. to about 700° C. Preferred temperatures may range from about 150° C. to about 600° C., and more preferred temperatures may range from about 200° C. to about 550° C. The reaction may be conducted at atmospheric pressure, super-atmospheric pressure or under vacuum. The vacuum pressure can be from about 5 torr (0.0966 psia) to about 760 torr (14.69 psia). Contact time of the HCFC-244bb with the catalyst may range from about 0.5 seconds to about 120 seconds, however, longer or shorter times can be used.

Preferably in such dehydrofluorination embodiments as described in this section, the conversion of the HCFC-244bb is at least about 10%, more preferably at least about 20%, and even more preferably at least about 30%. Preferably in such embodiments, the selectivity to HFO-1234yf, is at least about 70%, more preferably at least about 85% and more preferably at least about 95%.

In the preferred embodiment, the process flow may be in the down or up direction through a bed of the catalyst or horizontal direction. It may also be advantageous to periodically regenerate the catalyst after prolonged use while in place in the reactor. Regeneration of the catalyst may be accomplished by any means known in the art such as using an oxidizing agent such as $O_2$ or chlorine ($Cl_2$). For example, by passing air or air diluted with nitrogen over the catalyst at temperatures of from about 100° C. to about 400° C., preferably from about 200° C. to about 375° C., for from about 0.5 hour to about 3 days depending on the size of the reactor. The regeneration of the catalyst may also involve the use of a reducing agent such as $H_2$. Other reducing agents include, without limitation, $NH_3$ (ammonia), CO (carbon monoxide), $CH_4$ (methane); mixtures of these, including mixtures with hydrogen, optionally mixed with one or more inert diluents, may also be used. Inert diluents include without limitation nitrogen, helium, argon or neon and mixtures thereof.

In general, the effluent from the dehydrohalogenation reaction step, including any intermediate effluents that may be present in multi-stage reactor arrangements, may be processed to achieve desired degrees of separation and/or other processing. For example, in embodiments in which the reactor effluent comprises HFO-1234yf, the effluent will generally also include HCl and unreacted HCFC-244bb. Some portion or substantially all of these components of the reaction product may be recovered from the reaction mixture via any separation or purification method known in the art such as neutralization and distillation. It is expected that unreacted HCFC-244bb could be recycled, completely or partially, to improve the overall yield of the desired $CF_3CF=CH_2$ (HFO-1234yf). Optionally but preferably, hydrogen chloride is then recovered from the result of the dehydrochlorination reaction. Recovering of hydrogen chloride is conducted by conventional distillation where it is removed from the distillate.

Alternatively, HCl can be recovered or removed by using water or caustic scrubbers. When a water extractor is used HCl is removed as an aqueous solution. When caustic is used, HCl is removed from system as a chloride salt in aqueous solution.

In an alternate embodiment of the invention, dehydrohalogenation of HCFC-244bb can also be accomplished by reacting it with a strong caustic solution that includes, but is not limited to KOH, NaOH, $Ca(OH)_2$ and CaO at an elevated temperature. This is described in US Patent Publication No. 2011/0270000. In this case, the strength of the caustic solution is from about 2 wt % to about 100 wt %, more preferably from about 5 wt % to about 90 wt % and most preferably from about 10 wt % to about 80 wt %. The caustic to HCFC-244bb mole ratio preferably ranges from about 1:1 to about 2:1; more preferably from about 1.1:1 to about 1.5:1 and most preferably from about 1.2:1 to about 1.4:1. The reaction may be conducted at a temperature of from about 20° C. to about 100° C., more preferably from about 30° C. to about 90° C. and most preferably from about 40° C. to about 80° C. As above, the reaction may be conducted at atmospheric pressure, super-atmospheric pressure or under vacuum. The vacuum pressure can be from about 5 torr (0.0966 psia) to about 760 torr (14.69 psia). In addition, a solvent or phase transfer catalyst such as Aliquat 336 may optionally be used to help dissolve the organic compounds in the caustic solution. This optional step may be conducted using solvents that are well known in the art for said purpose. Thereafter, HFO-1234yf may be recovered from the reaction product mixture comprised of unreacted starting materials and by-products by any means known in the art, such as by extraction and preferably distillation. The mixture of HFO-1234yf and any by-products are passed through a distillation column. For example, the distillation may be preferably conducted in a standard distillation column at atmospheric pressure, super-atmospheric pressure or a vacuum. Preferably the pressure is less than about 300 psig, preferably less than about 200 psig and most preferably less than 150 psig. The pressure of the distillation column inherently determines the distillation operating temperature. Preferably in such dehydrofluorination embodiments as described in this section, the conversion HCFC-244bb is at least about 60%, more preferably at least about 75%, and even more preferably at least about 90%. Preferably in such embodiments, the selectivity to HFO-1234yf, is at least about 70%, more preferably at least about 85% and more preferably at least about 95%.

The following non-limiting examples serve to illustrate the invention.

EXAMPLE 1

A continuous liquid phase fluorination of the 2-chloro-3,3,3-trifluoropropene (HCFO-1233xf)+HF→2-chloro-1,1,1,2-tetrafluoropropane (HCFC-244bb) is demonstrated while continuously co-feeding 245cb. The fluorination catalyst for the experiment is $SbCl_5$.

3500 grams of $SbCl_5$ are contained in a Teflon™-lined liquid phase reactor (Teflon is a trademark of E.I. duPont de Nemours & Co) equipped with a catalyst stripper, a 2-inch ID (inside diameter) packed column with attached condenser whose function is to return entrained catalyst, some of the unreacted HF, and some of the unreacted 2-chloro-3,3,3-trifluoropropene (HCFO-1233xf) back to the reactor when the system is running in continuous reaction mode. The reactor is 2.75-inch ID×36-inch L (length) and is not equipped with a mixer/agitator. The reactor is heated to about 85° C.-87° C. The catalyst is then activated by the addition of 1500 grams of HF. HCl generated by the fluorination of the catalyst raises the reaction system pressure to about 100 psig where it will be controlled while running the continuous reaction. A continuous gaseous HF feed to the reactor is started first. The HF is pumped through a vaporizer and superheater prior to being bubbled into the liquid catalyst through a dip tube at a rate of 0.57 lb/hr, and when 1.0 lbs of HF has been added, the gaseous 245cb and liquid HCFO-1233xf organic co-feeds are started. They also enter the liquid catalyst by way of a dip tube. The HFC-245cb and HCFO-1233xf are fed continuously at rates of 0.11 lb/hr and 0.9 lb/hr respectively. The mole ratio of HF to 1233xf is 4.1:1 and the mole ratio of 245cb to 1233xf is 0.12:1. The reaction temperature is maintained at 85° C.-87° C. and the pressure is maintained at 100 psig. The HFC-245cb is gaseous at these conditions and is inert (i.e. does not react). As it bubbles into the liquid reaction mixture it dramatically increases mixing and because of high vapor pressure it helps to maintain the reactor pressure. It exits the reaction system through the top of the catalyst stripper helping to carry out the reaction product, HCFC-244bb, with it. The experiment is run continuously for 100 hours. The average conversion of HCFO-1233xf for the run is >96% and the selectivity to 244bb reaches is >98%.

EXAMPLE 2

The stream exiting the top of the catalyst stripper in Example 1 containing mainly HCFC-244bb, unreacted HF, and 245cb is fed to a conventional distillation column where 245cb is recovered and/or recycled back to the liquid phase reactor to aid in mixing, pressure maintenance, and product carrier.

EXAMPLE 3

A 2000 gallon commercial scale reactor is charged with antimony pentachloride catalyst. HCFO-1233xf and HF are fed continuously to the reactor vessel. HF is fed in excess. HFC-245cb is added as an additional component to aid mixing and to aid in volatilizing the product. HCFC-244bb, HF and HFC-245cb exit the vessel and are recovered.

What is claimed is:
1. A process to prepare 2-chloro-1,1,1,2-tetrafluoropropane (244bb) comprising:
(a) contacting 2-chloro-3,3,3,-trifluoropropene (1233xf) with HF in a reaction zone under conditions effective to form 244bb; and
(b) adding a co-feed species selected from the group consisting of CFC-12 (dichlorodifluoromethane), CFC-13 (chlorotrifluoromethane), CFC-14 (tetrafluoromethane), HCFC-22 (chlorodifluoromethane), HCFC-23 (trifluoromethane), HFC-32 (difluoromethane), HCC-40 (chloromethane) HFC-41 (fluoromethane), CFC-115 (chloropentafluoroethane), FC-116 (hexafluoroethane), HCFC-124 (2-chloro-1,1,1,2-tetrafluoroethane), HFC-125 (pentafluoroethane), HFC-134a (1,1,1,2-tetrafluoroethane), HFC-143a (1,1,1-trifluoroethane), HFC-152a (1,1-difluoroethane), HFC-161 (fluoroethane), FC-218 (octafluoropropane), HFC-227ea (1,1,1,2,3,3,3-heptafluoroethane), $SF_6$ (sulfur hexafluoride), and 1,1,1,2,2-pentafluoropropane (245cb) to the reaction zone to maintain a mole ratio of co-feed species to 1233xf of between about 0.005:1 to about 1:1.
2. The process of claim 1 wherein the co-feed species is 245cb.
3. The process of claim 2 wherein the 245cb:
(i) is a product of step (a) and is added back, in whole or in part, to the reaction zone in step (b) as recycle, or
(ii) is added to the reaction zone in step (b) as fresh 245cb, or
(iii) is added to the reaction zone as a combination (i) and (ii).
4. The process of claim 2 wherein the 245cb is added at a pressure of at least about 100 psig.
5. The process of claim 4 wherein the pressure is between about 100 psig and about 500 psig.
6. The process of claim 5 wherein the pressure is between about 120 psig to about 300 psig.
7. The process of claim 1 wherein the conditions effective include the presence of a fluorination catalyst.
8. The process of claim 1 wherein the mole ratio is between about 0.01:1 to about 0.5:1.
9. The process of claim 8 wherein the mole ratio is between about 0.04:1 to about 0.25:1.
10. A process to prepare 2-chloro-1,1,1,2-tetrafluoropropane (244bb) comprising feeding to a reaction zone 2-chloro-3,3,3,-trifluoropropene (1233xf), HF, and adding a co-feed species selected from the group consisting of CFC-12 (dichlorodifluoromethane), CFC-13 (chlorotrifluoromethane), CFC-14 (tetrafluoromethane), HCFC-22 (chlorodifluoromethane), HCFC-23 (trifluoromethane), HFC-32 (difluoromethane), HCC-40 (chloromethane) HFC-41 (fluoromethane), CFC-115 (chloropentafluoroethane), FC-116 (hexafluoroethane), HCFC-124 (2-chloro-1,1,1,2-tetrafluoroethane), HFC-125 (pentafluoroethane), HFC-134a (1,1,1,2-tetrafluoroethane), HFC-143a (1,1,1-trifluoroethane), HFC-152a (1,1-difluoroethane), HFC-161 (fluoroethane), FC-218 (octafluoropropane), HFC-227ea (1,1,1,2,3,3,3-heptafluoroethane), $SF_6$ (Sulfur hexafluoride), and 1,1,1,2,2-pentafluoropropane (245cb) under conditions effective to form 244bb wherein the mole ratio of co-feed specied to 1233xf in the reaction zone is between about 0.005:1 to about 1:1.
11. The process according to claim 10 wherein the co-feed species is 245cb.
12. The process of claim 10 wherein the mole ratio is between about 0.01:1 to about 0.5:1.
13. The process of claim 12 wherein the mole ratio is between about 0.04:1 to about 0.25:1.
14. A continuous liquid fluorination process to prepare 2-chloro-1,1,1,2-tetrafluoropropane (244bb) comprising:
a) contacting 2-chloro-3,3,3,-trifluoropropene (1233xf) and HF in a reactor in the presence of a fluorination catalyst under conditions effective to form 244bb and 1,1,1,2,2-pentafluoropropane (245cb);
b) recycling the 245cb back to the reactor at a pressure of at least about 100 psig.
15. The process of claim 14 wherein the pressure is between about 100 psig and about 500 psig.
16. The process of claim 15 wherein the pressure is between about 120 psig to about 300 psig.
17. The process of claim 14 wherein the co-feed species is 245cb and further comprising adding fresh 245cb to the reactor.
18. The process of claim 14 wherein the 245cb is added to maintain in the reactor a mole ratio of 245cb to 1233xf of between about 0.005:1 to about 1:1.
19. The process of claim 18 wherein the mole ratio is between about 0.01:1 to about 0.5:1.
20. The process of claim 19 wherein the mole ratio is between about 0.04:1 to about 0.25:1.
21. The process of claim 14 wherein the fluorination catalyst is selected from $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof.

22. A process to prepare 2,3,3,3-tetrafluoropropene (1234yf) comprising:
(a) providing a starting composition comprising at least one compound having a structure selected from Formula I, II and II:

$$CX_2=CCl-CH_2X \quad \text{(Formula I)}$$

$$CX_3-CCl=CH2 \quad \text{(Formula II)}$$

$$CX_3-CHCl-CH_2X \quad \text{(Formula III)}$$

wherein X is independently selected from F, Cl, Br and I, provided that at least one of X is not F;
(b) contacting said starting composition with HF in a first reaction zone under conditions effective to produce a first intermediate composition comprising 2-chloro-3,3,3-trifluoropropene (1233xf);
(c) contacting said first intermediate composition comprising 1233xf with HF in a second reaction zone in the presence of a fluorination catalyst under conditions effective to produce a second intermediate composition comprising 2-chloro-1,1,1,2-tetrafluoropropane (244bb) and 1,1,1,2,2-pentafluoropropane (245cb);
(d) recycling all or part of the 245cb formed in step (c) back to the second reaction zone; and
(e) dehydrochlorinating at least a portion of the 244bb to produce a reaction product comprising 1234yf.

23. The process of claim 22 wherein the 245cb in step (d) is recycled at a pressure of at least about 100 psig.

24. The process of claim 23 wherein the pressure is between about 100 psig and about 500 psig.

25. The process of claim 24 wherein the pressure is between about 120 psig to about 300 psig.

26. The process of claim 22 wherein the 245cb is recycled sufficient to maintain in the second reaction zone a mole ratio of 245cb to 1233xf of between about 0.005:1 to about 1:1.

27. The process of claim 26 wherein the mole ratio is between about 0.01:1 to about 0.5:1.

28. The process of claim 27 wherein the mole ratio is between about 0.04:1 to about 0.25:1.

* * * * *